United States Patent [19]

Bastian

[11] 4,024,266
[45] May 17, 1977

[54] 4H-BENZO[4,5]CYCLOHEPTA[1,2-B]THIOPHENES

[75] Inventor: Jean-Michel Bastian, Therwil, Switzerland

[73] Assignee: Sandoz Ltd., Basel, Switzerland

[22] Filed: Feb. 20, 1976

[21] Appl. No.: 659,779

[30] Foreign Application Priority Data

Feb. 26, 1975 Switzerland .................. 2437/75
Mar. 5, 1975 Switzerland .................. 2766/75

[52] U.S. Cl. .................. 424/267; 260/293.57
[51] Int. Cl.² .................. C07D 409/04
[58] Field of Search .......... 260/293.57; 424/267

[56] References Cited
UNITED STATES PATENTS 3,491,103  1/1970  Jucker et al. ............ 260/293.4

Primary Examiner—G. Thomas Todd
Attorney, Agent, or Firm—Gerald D. Sharkin; Robert S. Honor; Thomas O. McGovern

[57] ABSTRACT

This invention provides new compounds of formula I,

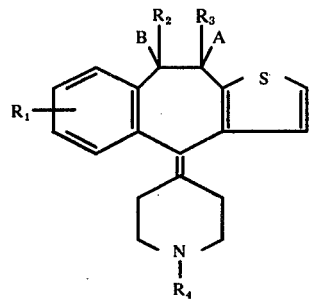

wherein
$R_1$ is hydrogen, halogen of an atomic number of from 9 to 35, or alkyl of 1 to 4 carbon atoms,
$R_2$ is alkyl of 1 to 4 carbon atoms,
$R_4$ is alkyl of 1 to 4 carbon atoms, and either
i.
   $R_3$ is hydrogen or alkyl of 1 to 4 carbon atoms, and
   A and B together form a bond, or
ii.
   $R_3$ is hydrogen, and
   A and B are both hydrogen,
useful as LH inhibitors and antidepressants.

21 Claims, No Drawings

I

4H-BENZO[4,5]CYCLOHEPTA[1,2-B]THIOPHENES

The present invention relates to 4H-benzo[4,5]cyclohepta[1,2-b]thiophene derivatives.

The present invention provides the following compounds of formula I,

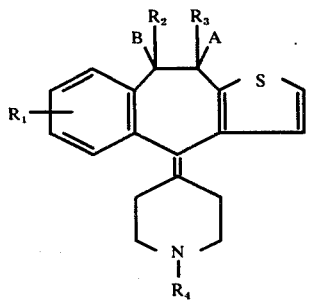

I wherein
- $R_1$ is hydrogen, halogen of an atomic number of from 9 to 35, or alkyl of 1 to 4 carbon atoms,
- $R_2$ is alkyl of 1 to 4 carbon atoms,
- $R_4$ is alkyl of 1 to 4 carbon atoms, and either
  (i)
    $R_3$ is hydrogen or alkyl of 1 to 4 carbon atoms, and
    A and B together form a bond, or
  (ii)
    $R_3$ is hydrogen, and
    A and B are both hydrogen.

$R_1$ is preferably hydrogen; otherwise $R_1$ is preferably in the 6- or 7-position of the benzocycloheptathiophene moiety. If $R_1$ is halogen, it is preferably chlorine. If $R_1$, $R_2$, $R_3$ or $R_4$ is alkyl, then it is preferably of 1 to 3 carbon atoms, especially methyl.

Especially preferred are compounds of formula I, wherein $R_1$ is hydrogen or chlorine, preferably in the 7-position of the benzocycloheptathiophene moiety, $R_2$ and $R_4$ are each alkyl of 1 to 3 carbon atoms, especially methyl, and $R_3$ is hydrogen, methyl or ethyl.

The present invention provides a process for the production of a compound of formula I which comprises (a) removing water from a compound of formula II,

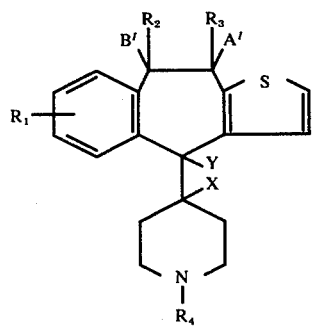

II wherein
$R_1$, $R_2$, $R_3$ and $R_4$ are as defined above, and either
  i
    $A^I$ is hydroxyl, and
    $B^I$ is hydrogen, and
    X and Y are together a bond, or ii
    $A^I$ and $B^I$ are together a bond, or,
    provided that $R_3$ is hydrogen, $A^I$ and
    $B^I$ may each be hydrogen, and X is hydrogen, and
    Y is hydroxyl, or (b) for the production of a compound of formula Ia,

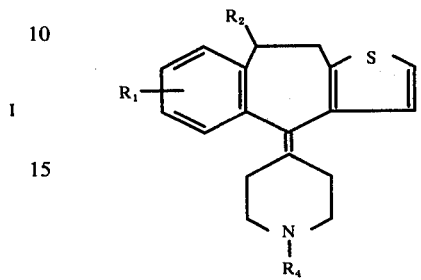

Ia wherein $R_1$, $R_2$ and $R_4$ are as defined above, reducing a compound of formula III,

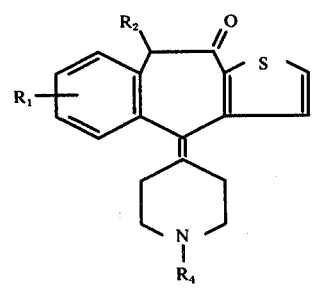

III wherein $R_1$, $R_2$ and $R_4$ are as defined above.

Process variant (a) may be effected in conventional manner for the removal of water from analogous carbinols, e.g. using a suitable water-removing agent. The reaction may be carried out conveniently in an inert organic solvent, e.g. a lower alkanol. As water-removing agents may be used for example mineral acids, strong organic acids, acid anhydrides or acid halides such as acetic anhydride or thionyl chloride. Examples of mineral acids are hydrochloric acid, conveniently hydrogen chloride in an alkanol, or concentrated hydrogen chloride/acetic acid. Examples of organic acids are trifluoroacetic acid or benzenesulphonic acid. The reaction temperature may be conveniently from about 0° to about 100° C.

Process variant (b) may be effected in conventional manner for the reduction of a carbonyl group to a methylene group, e.g. using the method of Clemmensen or Wolff-Kishner or a modification thereof. According to Clemmensen's method amalgamated zinc in hydrochloric acid may be used conveniently in the presence of an inert organic solvent, e.g. an aromatic hydrocarbon solvent such as toluene or a water-miscible solvent such as a lower alkanol, acetic acid or a suitable ether such as dioxane. According to Wolff-Kishner's method the compound of formula III is converted first into the hydrazone which is then treated with a strong base, e.g. an alkali metal hydroxide or alcoholate. The Wolff-Kishner reduction is conveniently effected according to the Huang-Minlon variant, e.g. treatment of a compound of formula III with hydrazine hydrate in the presence of an alkali metal hydroxide in a water-miscible high-boiling organic solvent, e.g. a polyalcohol such as di- or tri-ethylene glycol, at a temperature of from about 50° C. The water formed is distilled off from the reaction mixture which is then heated for about a further 3 to 6 hours at a temperature of about 200° to about 250° C. In a further method described in Chem. Ind. 1964, 153, the compound of formula III is converted with tosyl hydrazine into the corresponding tosyl hydrazone which is then reduced with sodium borohydride.

Free base forms of compounds of formula I may be converted into acid addition salt form in conventional manner and vice versa. A suitable inorganic salt is the hydrochloride. A suitable organic salt is the maleate, malate or hydrochloride.

The starting materials may be produced as follows:
-methyl-
(a') Compounds of formula IIa,

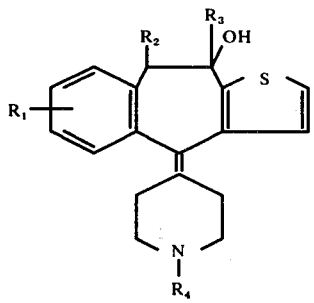

wherein $R_1$ to $R_4$ are as defined above, may for example be obtained by reacting a compound of formula III,

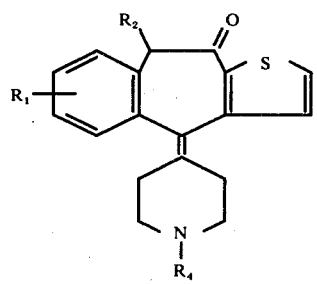

wherein $R_1$, $R_2$ and $R_4$ are as defined above, with a compound of formula IV,

R₃—Z    IV wherein
$R_3$ is defined as above, and
Z is lithium or -Mg-Hal, wherein Hal is chlorine, iodine or bromine,
in conventional manner, e.g. under conditions of a Grignard reaction.

(b') Compounds of formula III may for example be produced by alkylating a compound of formula V,

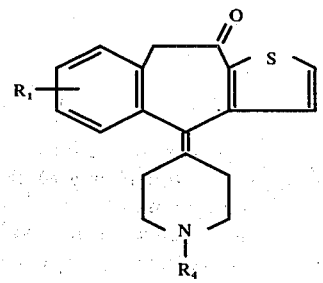

wherein $R_1$ and $R_4$ are as defined above, in conventional manner, e.g. using the appropriate alkyl halide.

(c') Compounds of formula IIb,

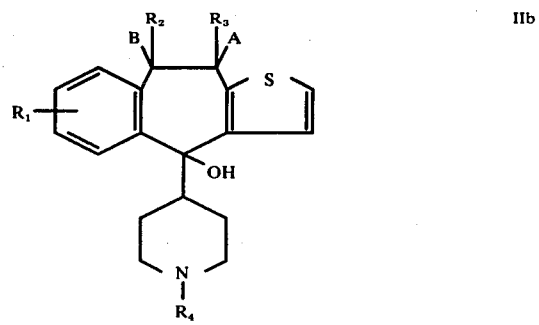

wherein $R_1$ to $R_4$ and A and B are as defined above, may for example be obtained by reacting a compound of formula VI,

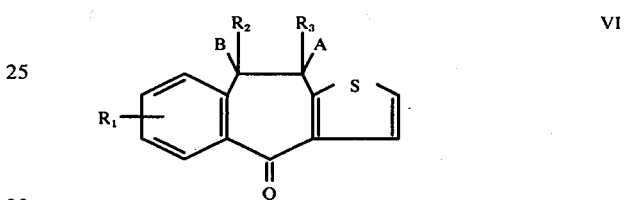

wherein $R_1$ to $R_3$, A and B are as defined above, with a compound of formula VII,

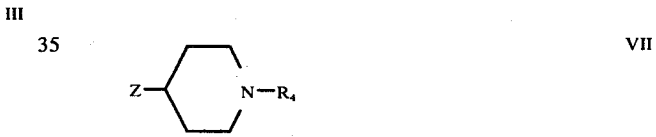

wherein $R_4$ and Z are as defined above, in conventional manner, e.g. under conditions of a Grignard reaction.

(d') Compounds of formula VIa,

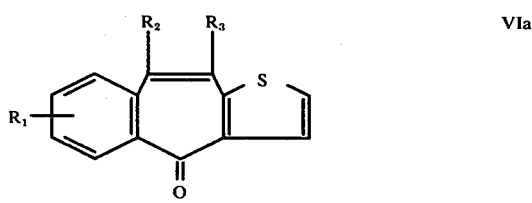

wherein $R_1$ to $R_3$ are as defined above, may be obtained by (i) mono-brominating a compound of formula VIb,

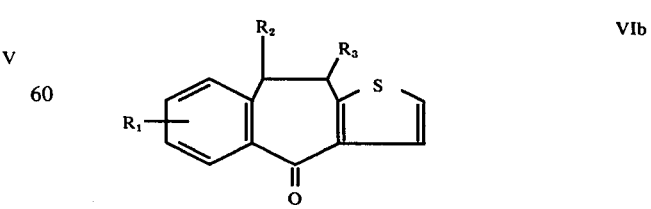

wherein $R_1$, $R_2$ and $R_3$ are as defined above, in conventional manner with N-bromosuccinimide to give a product with bromine in the 9 or 10 position of the benzocycloheptathiophene ring, and ii) splitting off hydrogen bromide from this reaction product.

(e') Compounds of formula VIb may be obtained by (i) catalytically hydrogenating a compound of formula VIII,

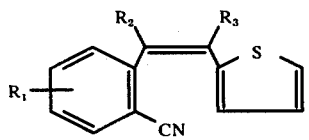

wherein $R_1$ to $R_3$ are as defined above,
(ii) hydrolysing the cyano group to the carboxyl group in the reaction product, and
(iii) cyclising the resulting acid, or a reactive acid derivative thereof, preferably in the presence of polyphosphoric acid.

(f') Compounds of formula VIII may be obtainable for example by reacting a compound of formula IX,

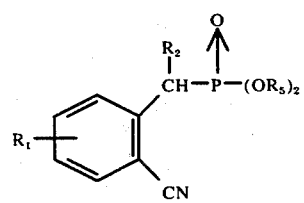

wherein
$R_1$ and $R_2$ are as defined above, and
$R_5$ is lower alkyl,
with a compound of formula X,

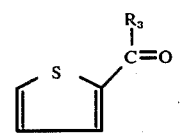

wherein $R_3$ is as defined above, under the conditions of Horner's variant of the Witting reaction.

Insofar as the production of any starting material is not particularly described these compounds are known or may be produced and purified in accordance with known processes or in a manner analogous to processes described herein or to known processes.

In the following Examples all temperatures are in Centigrade and are uncorrected.

EXAMPLE 1

4-(9-Methyl-4H-benzo[4,5]cyclohepta[1,2-b]thiophen-4-ylidene)-1-methylpiperidine

[process variant a)]

A solution of 17.0 g of 9,10-dihydro-9-methyl-4-(1-methyl-4-piperidylidene)-4H-benzo[4,5]cyclohepta[1,2-b]thiophen-10-ol (mixture of α and β isomers) in 300 ml of 5N hydrogen chloride in isopropanol was boiled for 20 minutes and then concentrated. The residue was taken up in water. The mixture was made alkaline with concentrated sodium hydroxide solution and then extracted with benzene. The benzene extracts were washed with water, dried over sodium sulphate and concentrated. The title compound was obtained as an oil which was converted in acetone/ether into the hydrochloride. M.Pt.-sintering from 182°; decomposition from 190°.

The starting material was obtained as follows:
(a) 24.5 g of 4-(1-methyl-4-piperidylidene)-4H-benzo[4,5]cyclohepta[1,2-b]thiophen-10(9H)-one were dissolved in 750 ml of boiling cyclohexane. The mixture was cooled to 50° and whilst this temperature was maintained 10.7 g of potassium tert-butylate were added. The resulting suspension was cooled to 20°, and whilst this temperature was maintained 12.4 g of methyl iodide were slowly added dropwise. The mixture was stirred for a further 1 hour and then treated with 100 ml of water and 100 ml of benzene. The organic phase was separated off and evaporated to yield crude 9-methyl-4-(1-methyl-4-piperidylidene)-4H-benzo[4,5]cyclohepta[1,2-b]thiophene-10(9H)-one as an oil which can be used further in crude form (M.Pt. of hydrogen fumarate 213°–215° from ethanol).

(b) 25.0 g of the crude above-mentioned 9-methyl ketone in 350 ml of ethanol were reduced with 3.0 g of sodium borohydride dissolved in 13 ml of water and 0.4 ml of 40% w/v aqueous sodium hydroxide. [Reaction time 4 hours at 40° and then 1 hour at room temperature]. After 35 ml of methanol had been added, the reaction mixture was boiled for 30 minutes, and then concentrated. The residue was dissolved in chloroform and water. The organic phase was worked up to give the isomers of 9,10-dihydro-9-methyl-4-(1-methyl-4-piperidylidene)-4H-benzo[4,5]cyclohepta[1,2-b]thiophen-10-ol; α-isomer M.Pt. 220°–222°; β-isomer 236°–237°.

EXAMPLE 2

4-(9,10-Dimethyl-4H-benzo[4,5]cyclohepta[1,2-b]thiophen-4-ylidene)-1-methylpiperidine In analogous manner to Example 1, 9.5 g of 9,10-dihydro-9,10-dimethyl-4-(1-methyl-4-piperidyliden)-4H-benzo[4,5]cyclohepta[1,2]thiophen-10-ol in 180 ml of 5N hydrogen chloride in isopropanol were converted into the title compound in hyrochloride form. M.pt. 266°–267° (crystallized from acetone).

The starting material was obtained as follows:
(a) A solution of 11.0 g of 9-methyl-4-(1-methyl-4-piperidylidene)-4H-benzo[4,5]cyclohepta[1,2-b]thiophen10(9H)-one in 150 ml of benzene was added dropwise in a nitrogen atmosphere at 25°–30° to a solution of 150 ml of diethylether and 43 ml of 2 molar methyllithium in diethylether. The reaction mixture was stirred for 3 hours at room temperature and then treated with 500 ml of 20% w/v aqueous ammonium chloride. The organic phase was separated off and worked up to give solid 9,10-dihydro9,10-dimethyl-4-(1-methyl-4-piperidylidene)-4H-benzo[4,5]cyclohepta[1,2-b]thiophen-10-ol which was further reacted in crude form.

In analogous manner to Example 1 including steps (a) and (b) and Example 2 including step a) the following 4H-benzo[4,5]cyclohepta[1,2-b]thiophene derivatives of formula I are produced, wherein:

| Ex. No. | $R_1$ | $R_2$ | $R_3$ | $R_4$ | A+B | Physical. Constants |
|---|---|---|---|---|---|---|
| 2A | 7-Cl | $CH_3$— | H | $CH_3$— | Bond | M.Pt.:from 190° S** from 200° Z*** |

-continued

| Ex. No. | R₁ | R₂ | R₃ | R₄ | A+B | Physical. Constants |
|---|---|---|---|---|---|---|
| 2B | H | CH₃— | C₂H₅— | CH₃— | " | M.Pt.:HCl*:235–236° |
| 2C | H | CH₃\CH—/CH₃ | H | CH₃— | " | M.Pt.:from 203° Z*** |
| 2D | H | CH₃— | CH₃ | C₂H₅ | " | Rf Δ 5,9 |
| 2E | 7-Cl | CH₃— | CH₃— | CH₃— | " | Rf Δ 5,7 |
| 2F | H | CH₃\CH—/CH₃ | CH₃— | CH₃ | " | Rf Δ 6,0 |

**S = Sintering point
***Z = Decomposition point
*HCl = Hydrochloride
Δ Thin layer chromatogram: Silica gel absorbent. Eluant: benzene/ethanol/(conc.) aqueous ammonia 84:15:1.

EXAMPLE 3

4-(9,10-dihydro-9-methyl-4H-benzo[4,5]cyclohepta[1,2-b]thiophen-4-ylidene)-1-methylpiperidine A solution of 12.0 g of 9,10-dihydro-9-methyl-4-(1-methyl-4-piperidyl)-4H-benzo[4,5]cyclohepta[1,2-b]thiophen-4-ol in 180 ml of isopropanol and 180 ml of 7N hydrogen chloride in isopropanol was boiled for 3 hours, and concentrated to dryness. The residue was taken up in 100 ml of water. The mixture was made alkaline with concentrated aqueous sodium hydroxide and then extracted with methylene chloride. The extracts were washed with water, dried over potassium carbonate and concentrated. The title compound obtained as an oil was converted in ethanol into the hydrogen malate (M.Pt. of hydrogen malate: 193°–194° from ethanol).

The starting material was obtained as follows:

(a) A solution of 73.0 g of 2-thiophenaldehyde and 170 g of diethyl-1-(o-cyanophenyl)ethylphosphonate in 800 ml of anhydrous dimethyl formamide was added dropwise in a nitrogen atmosphere at 20°–30°to a suspension of 39.0 g of sodium methylate in 500 ml of anhydrous dimethyl formamide. The mixture was further stirred for 1 hour at 40°, cooled to 10°–15° and treated with ca. 5 l of icewater. Working up gave 2-[1-(2-thienyl)-2-propenyl]benzonitrile, B.Pt. (0.1 to 0.2 mm Hg) = 200°–210°.

(b) A solution of 125.0 g of the product obtained in step (a) in 1,250 ml of ethanol was hydrogenated in the presence of 32.0 g of 5% w/w palladium on aluminium oxide for 24 hours at 100° under 15 atmospheres of hydrogen to afford 2-[1-(2-thienyl)-2-propyl]benzonitrile, B.Pt. (0.1 mm Hg) 205°–210°.

(c) A solution of 110 g of the product obtained in step b) in 100 ml of diethyleneglycol monomethyl ether was added slowly dropwise to a mixture of 220 g of potassium hydroxide in 350 ml of diethyleneglycol monomethyl ether at 180°. The mixture was stirred for 3 hours at 180°, cooled to 70° and afforded after working up 2-[1-(2-thienyl)2-propyl]benzoic acid, M.Pt. 94°–95° C.

(d) A mixture of 12.0 g of the acid obtained in step c) and 120 g of polyphosphoric acid was stirred for 2hours at 70° to 80°, then shaken with 500 ml of water, giving after working up 9,10-dihydro-9-methyl-4H-benzo[4,5]cyclohepta[1,2-b]thiophen-4-one. B.Pt. (0.05 mm Hg) 190°–198°.

(e) 2.4 g of magnesium previously activated with iodine were reacted with 12.0 g of 4-chloro-1-methylpiperidine in 100 ml of anhydrous tetrahydrofuran over 2 hours at reflux temperature. The reaction mixture was cooled to 10°, and reacted with a solution of 9,10-dihydro-9-methyl4H-benzo[4,5]cyclohepta[1,2-b]thiophen-4-one in 70 ml of anhydrous tetrahydrofuran. After 1 hour of stirring at room temperature and 1 hour at reflux temperature the reaction mixture was cooled and treated with 150 ml of 20% w/v of aqueous ammonium chloride. The organic phase was separated off and worked up to give as a thick oil 9,10-dihydro-9-methyl-4-(1-methyl-4-piperidyl)-4H-benzo[4,5]cyclohepta[1,2-b]thiophen-4-ol which was further reacted as such.

In analogous manner to Example 3 including steps (a) to (e), the compounds of Examples 1, 2 and 2A to 2F as well as the following compounds of formula I are obtained, wherein:

| Ex. No. | R₁ | R₂ | R₃ | R₄ | A,B | Physical Constants |
|---|---|---|---|---|---|---|
| 3A | 7-Cl | CH₃— | H | CH₃— | each H | M.Pt.:135°–137° |
| 3B | H | CH₃— | H | C₂H₅— | " | Rf Δ:5,8 |
| 3C | H | C₂H₅— | H | CH₃— | " | Rf Δ:7,2 |

ΔSee above table.

EXAMPLE 4

4-(9,10-dihydro-9-methyl-4H-benzo[4,5]cyclohepta[1,2-b]thiophen-4-ylidene)-1-methylpiperidine

[process variant b)]

16.0 ml of hydrazine hydrate and 15.5 g of potassium hydroxide were added to a solution of 25.0 g of 9-methyl-4-(1-methyl-4-piperidylidene)-4H-benzo[4,5]cyclohepta[1,2-b]thiophen-10(9H)-one in 350 ml of diethylene glycol. The reaction mixture was warmed and stirred for 1 hour to 150° and 3 hours to 205°–210°. The mixture was cooled to room temperature and treated with 2 liters of water. The aqueous suspension was extracted 3 times with methylene chloride. The extracts were washed with water and a saturated sodium chloride aqueous solution, dried over sodium sulphate, and concentrated. The oily residue was dissolved in ethanol, decolourized with charcoal and converted into the hydrogen malate (M.Pt. 193°–194° from ethanol).

In analogous manner to Example 4 the compounds of formula Ia of Examples 3A to 3C may also be produced by reducing the corresponding compounds of formula III.

It will be appreciated that compounds of formula I, wherein $R_1$ is alkyl, and in the 5, 6 or 8 position may be made in analogous manner to that disclosed in Examples 1, 2, 3 and 4.

The compounds of formula I exhibit pharmacological activity. In particular they exhibit anti-depressant activity as indicated in standard tests:

(1) In one standard test in accordance with the method of G. Stille [Arz. Forsch. 14, 534-7 (1964)] an antagonism of the ptosis and catalepsy induced in rats by tetrabenzine is observed. The compounds are administered i.p. at from about 5 to about 50 mg/kg animal body weight. The tetrabenazine is administered i.p. 30 minutes after the administration of the compounds at a dosage of 10 mg/kg animal body weight.

(2) In a further test in accordance with the method of Gillespie and Muir (Brit. J. Pharmacol. 1967, 30, 78 and 1970, 40, 257), the compounds potentiate the noradrenaline-induced pressor response in the pithed rat. The noradrenaline is administered i.v. at a dosage of 1 microgram per rat. The increased blood pressure in the carotid artery is recorded.

In this test the compounds are administered i.v. at from about 0.005 to about 0.5 mg/kg animal body weight.

(3) In a further standard test based on the method of Spencer, P.S.J. (1965) Brit. J. Pharmacol. 25, 442 an antagonism of oxotremorine-induced tremors and hypothermia is observed. In this test mice are acclimatised to laboratory conditions overnight. 2 mg/kg animal body weight of atropine methyl nitrate is administered s.c.; 10 minutes later the test substance is administered. 20 minutes later rectal temperatures are measured with a probe. The presence of tremors is also assessed. Oxotremorine at a dose of 0.5 mg/kg animal body weight is then administered s.c.. The hypothermia and inhibition of tremors are then determined.

The compounds are therefore useful in the treatment of exogenous and exogenous depressions.

For the above mentioned use the dosage will, of course, vary depending on the compound employed, mode of administration and therapy desired. However, in general, satisfactory results are obtained when administered at a daily dosage of from 0.01 mg to about 50 mg per kg animal body weight, conveniently given in divided doses 2 to 4 times a day or in sustained release form. For the larger mammal the daily dosage is in the range from about 0.5 to about 5 mg/kg and the total daily dosage is in the range from about 3 to about 300 mg, and dosage forms suitable for oral administration comprise from about 0.7 mg to about 150 mg of the compounds admixed with a solid or liquid pharmaceutical carrier or diluent.

An example of a daily dosage is from 0.05 to 20 mg/kg, conveniently 3 to 150 mg to be administered in divided dosages containing from 0.7 to 75 mg.

The Example 1 compound is the most interesting compound. pro-oestrus an

Furthermore in one standard test in adult female rats on s.c. and p.o. administration of about 0.05 to about 0.5 mg/kg animal body weight of the compounds at noon of the prooestrus day both in inhibition of the expected increase in the level of luteinizing hormone in the blood serum and an inhibition of the expected ovulation during the following night, are observed.

The compounds are therefore further useful as agents for inhibiting cyclic (pre-ovulatory) secretion of the luteinizing hormone and therefore for the inhibition of gonadotropin secretion, e.g. for use inter alia as contraceptives for female animals, in the treatment of prostate hypertropy, menopausal syndrome, precocious puberty, and endometriosis.

For the above mentioned use the dosage will, of course, vary depending on the compound employed, mode of administration and therapy desired. However, in general, satisfactory results are obtained when administered at a daily dosage of from 0.01 mg to about 50 mg per kg animal body weight, conveniently given in divided doses 2 to 4 times a day or in sustained release form. For the larger mammal, the total daily dosage is in the range from about 0.5 to about 100 mg, and dosage forms suitable for oral administration comprise from about 0.1 mg to about 50 mg, e.g. to 7 mg, of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

In a group of compounds $R_3$ is hydrogen.

In another group of compounds A and B form together a bond.

Further acids for salt formation include acetic, hydrobromic and fumaric acids.

What is claimed is:

1. A compound of formula I,

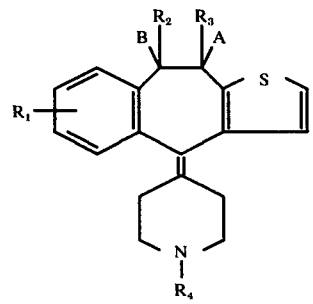

wherein
$R_1$ is hydrogen, halogen of an atomic number of from 9 to 35, or alkyl of 1 to 4 carbon atoms,
$R_2$ is alkyl of 1 to 4 carbon atoms,
$R_4$ is alkyl of 1 to 4 carbon atoms, and either
(i)
$R_3$ is hydrogen or alkyl of 1 to 4 carbon atoms, and
A and B together form a bond, or
(ii)
$R_3$ is hydrogen, and
A and B are both hydrogen,
in free base form or in pharmaceutically acceptable acid addition salt form.

2. A compound of claim 1, wherein A and B together form a bond.

3. A compound of claim 1, wherein A and B together are both hydrogen.

4. The compound of claim 1 which is 4-(9-methyl4H-benzo[4,5]-cyclohepta[1,2-b]thiophen-4-ylidene)-1-methylpiperidine.

5. The compound of claim 1 which is 4-(9,10-dimethyl-4H-benzo[4,5]cyclohepta[1,2-b]thiophen-4-ylidene)-1-methylpiperidine.

6. The compound of claim 1 in which $R_1$, $R_2$, $R_3$ and $R_4$ are respectively 7—Cl, $CH_3$—, H and $CH_3$— and A + B is a second bond.

7. The compound of claim 1 in which $R_1$, $R_2$, $R_3$ and $R_4$ are respectively H, $CH_3$—, $C_2H_5$—, $CH_3$— and A + B is a second bond.

8. The compound of claim 1 in which $R_1$, $R_2$, $R_3$ and $R_4$ are respectively

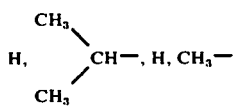

and A + B is a second bond.

9. The compound of claim 1 in which $R_1$, $R_2$, $R_3$ and $R_4$ are respectively H, $CH_3$—, $CH_3$, $C_2H_5$ and A + B is a second bond.

10. The compound of claim 1 in which $R_1$, $R_2$, $R_3$ and $R_4$ are respectively 7—Cl, $CH_3$—, $CH_3$—, $CH_3$— and A + B is a second bond.

11. The compound of claim 1 in which $R_1$, $R_2$, $R_3$ and $R_4$ are respectively

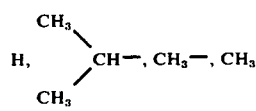

and A + B is a second bond.

12. The compound of claim 1 which is 4-(9,10-dihydro-9-methyl-4H-benzo[4,5]cyclohepta[1,2-b]thiophen-4-ylidene)-1-methylpiperidine.

13. The compound of claim 1 in which $R_1$, $R_2$, $R_3$, $R_4$, A and B are respectively 7—Cl, $CH_3$—, H, $CH_3$—, H and H.

14. The compound of claim 1 in which $R_1$, $R_2$, $R_3$, $R_4$, A and B are respectively H, $CH_3$—, H, $C_2H_5$, H and H.

15. The compound of claim 1 in which $R_1$, $R_2$, $R_3$, $R_4$, A and B are respectively H, $C_2H_5$—, H, $CH_3$, H and H.

16. A pharmaceutical composition comprising a therapeutically effective amount of a compound of claim 1 in association with a pharmaceutical carrier or diluent.

17. A pharmaceutical composition according to claim 16 useful in treating depression comprising 3 to 300 milligrams of the compound or a pharmaceutically acceptable acid addition salt thereof in association with a pharmaceutical carrier or diluent.

18. A pharmaceutical composition according to claim 16, comprising 0.7 to 150 milligrams of the compound per unit dosage.

19. A method of treating depressions in animals which comprises administering a therapeutically effective amount of a compound of claim 1 to an animal in need of such treatment.

20. A method according to claim 19 in which 3 to 300 milligrams of the compound are administered daily.

21. A method according to claim 19 in which 0.7 to 150 milligrams of the compound are administered per unit dose.

* * * * *